United States Patent [19]

Wong et al.

[11] Patent Number: 5,393,879
[45] Date of Patent: Feb. 28, 1995

[54] FRUCTOSYL C-GLYCOSIDE NUCLEOSIDE ANALOGS

[75] Inventors: Chi-Huey Wong, Rancho Santa Fe, Calif.; Kun-Chin Liu, New Haven, Conn.

[73] Assignee: The Scripps Research Institute, La Jolla, Calif.

[21] Appl. No.: 931,014

[22] Filed: Aug. 17, 1992

[51] Int. Cl.$^6$ .............. C07H 7/00; C07H 7/06
[52] U.S. Cl. ................... 536/29.2; 544/265
[58] Field of Search ........ 536/29.2, 26.1, 26.7, 536/26.74, 26.8, 27.6, 27.81, 28.1, 28.4, 28.53

[56] References Cited

U.S. PATENT DOCUMENTS

| | | | |
|---|---|---|---|
| 3,928,319 | 12/1975 | Jenkins et al. | 536/29.2 |
| 4,161,582 | 7/1979 | Weigle et al. | 536/29.2 |
| 4,619,996 | 10/1986 | Cook et al. | 536/55.3 |
| 4,656,260 | 4/1987 | Kato et al. | 536/55 |
| 5,137,876 | 8/1992 | Mac Coss et al. | 514/23 |
| 5,229,523 | 7/1993 | Wong et al. | 548/544 |
| 5,276,120 | 1/1994 | Wong et al. | 546/148 |

OTHER PUBLICATIONS

Zinsser Microbiology, 20th ed., Joklik et al., eds., Appleton & Lange, Norwalk, Conn. (1992), pp. 856–857.

*Primary Examiner*—John W. Rollins
*Assistant Examiner*—Gary L. Kunz
*Attorney, Agent, or Firm*—Welsh & Katz, Ltd.

[57] ABSTRACT

Nucleoside and nucleotide analogs corresponding to structural Formula I, below, are disclosed, in that structural formula, B is a

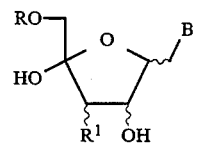

purine base attached at the 9-position or pyrimidine base, attached at the 1-position R is hydrogen or $PO_3=M^{+2}$, where $M^{+2}$ is a mono- or divalent cation, and $R^1$ is hydrogen or hydroxyl.

5 Claims, No Drawings

FRUCTOSYL C-GLYCOSIDE NUCLEOSIDE ANALOGS

This invention was made with government support under Contract No. GM 44154 awarded by the National Institutes of Health. The government has certain rights in the invention.

TECHNICAL FIELD

The present invention relates to the synthesis of nucleoside analogs, and more particularly to 1-deoxy-1-(purinyl or pyrimidinyl) fructose derivatives and analogs, their 6-phosphates and the syntheses of those compounds.

BACKGROUND ART

Nucleosides and their phosphorylated derivatives, nucleotides, are the constituents of DNA or RNA, as well as being biological signaling molecules as is GDP. Nucleoside analogues with modifications at the carbohydrate or base portion have been used extensively as antibiotics and as biological probes. Suhadolnik, *Nucleoside Antibiotics*, J. Wiley, New York, (1970); Suhadolnik, *Nucleoside as Biological Probes*, J. Wiley, New York, (1979); *Nucleoside Analogues; Chemistry biology and Medicinal Applications*, Walk et al., eds., NATO Advanced Study Institute Series: Plenum, New York, Vol. 26, (1979); Thiers, *Dermatologic Clinics,* 8:583–587 (1990); O'Brien et al., *Drugs,* 37:233–309 (1989); Shimada et al., 28th Interscience Conference on Antimicrobial Agents and Chemotherapy, Abstract 1008, Los Angeles, Calif. (1988); Norbeck et al., *Tetrahedron Lett.* 6263 (1989); Ezzel, *Natural,* 326,430; DeClerq, *Trends Pharmacol. Sci.,* 87:339–45 (1987). For example, several nucleoside analogs and purine and pyrimidine base derivatives such as 2-chloro-2'-deoxyadenosine, dideoxyinosine, dideoxycytidine, dideoxythymidine, dideoxyguanidine, 9-[(2-hydroxymethoxy)methyl]guanine (acylovir) and 9-(3,4-dihydroxybutyl)guanine and the like have found medical utility in treating various disease states such as hairy cell leukemia, as well as being useful as inhibitors of DNA polymerase enzymes and polynucleotide chain terminating reagents for DNA or RNA sequencing studies.

Nucleosides are traditionally synthesized by chemical methods. *Nucleoside Analogues; Chemistry, biology and Medicinal Applications*, Walk et al., eds., NATO Advanced Study Institute Series: Plenum, New York, Vol. 26, (1979). Enzymatic synthesis of nucleosides based on nucleoside phosphorylase or deoxyribosyl transferase has recently been developed. Krenitsky et al., *J. Med. Chem.,* 29:138–143 (1986); Utagawa et al., *Agric. Biol. Chem.,* 49:3239 (1985); Krenitsky et al., *Carbohydr. Res.,* 97:139–146 (1981); Krenitsky et al., *Biochemistry,* 20:3615–3621 (1981); Hennen et al., *J. Org. Chem.,* 54:4692 (1989); Betbeder et al., *Nucleosides and Nucleotides,* 10:465–468 (1991); Hutchinson, *TIBTECH,* 8:348 (1990).

One of the drawbacks in use of such compounds is in the synthesis of the purine or pyrimidine group linked various sugar rings (furanoses). Thus, although nature prepares each of the furanose derivatives, only ribosyl and 2-deoxyribosyl furanoses are naturally found bonded to nucleic acid bases as nucleosides. In addition, all of the naturally occurring nucleosides and nucleotides contain a purine or pyrimidine nitrogen atom bonded directly to the 1-position of the ribosyl or 2-deoxyribosyl ring; i.e., adjacent to the ring oxygen atom.

It would therefore be beneficial if synthetic routes were available to prepare purine and pyrimidine derivatives bonded to a furanose having other than a ribosyl or deoxyribosyl ring, and bonded at a position other than adjacent the ring oxygen atom. The disclosure that follows describes such syntheses.

BRIEF SUMMARY OF THE INVENTION

A nucleoside or nucleotide analog of structural Formula I, below, is contemplated, wherein B is a purinyl or pyrimidyl base group, R is hydrogen or $PO_3=M^{+2}$, where $M^{+2}$ is a mono- or divalent cation, and $R^1$ is hydrogen or hydroxyl. It is preferred that $R^1$ be hydroxyl, so that a preferred nucleoside or nucleotide analog corresponds to structural Formula II, below.

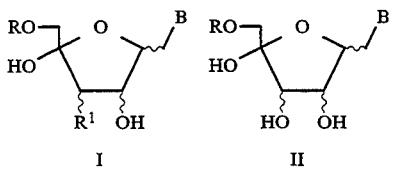

Adenine is preferred purine, and a preferred compound of structural Formula II corresponds to structural Formula III, where A is a 9-adeninyl group.

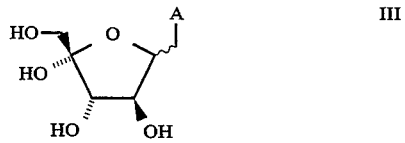

A process for preparing a nucleotide 6'-phosphate analog of structural Formula IV, below, wherein B and $R^1$ are as before defined, is also contemplated.

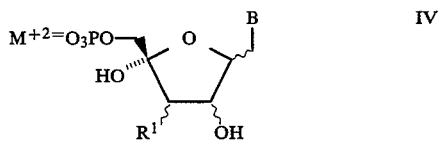

In accordance with this process, a N-3-(purine or pyrimidine base)-2-hydroxypropanal is admixed with dihydroxyacetone phosphate or acetone monohydroxy phosphate in an aqueous medium in the presence of a catalytic amount of an aldolase enzyme to form a reaction mixture. The reaction mixture so formed is maintained for a time period sufficient for the nucleotide 6'-phosphate analog to form. This process also defines a process for using an aldolase enzyme to condense the above, substituted propanal and hydroxyacetone phosphates to form a compound of structural Formula IV.

Exemplary aldolases include fructose-1,6-diphosphate (FDP) aldolase, rhamulose-1-phosphate (Rham-1-P) aldolase, fuculose-1-phosphate (Fuc-1-P) aldolase, and tagatose-1,6-diphosphate (TDP) aldolase.

Removing the phosphate group by any well known means provides the corresponding nucleoside analog of structural Formula I, where R is hydrogen. That nucleoside is illustrated by the structural formula shown below, where B and $R^1$ are as defined previously.

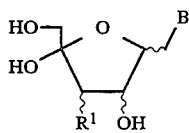

The phosphate group is preferably removed enzymatically. Exemplary enzymes for such removal are the acid and basic phosphatases, as are well known.

DETAILED DESCRIPTION OF THE INVENTION

I. The Compounds

A compound of the invention is a 1-deoxy-1-(9-purinyl or 1-pyrimidyl)fructose derivative or 6-phosphate, or an analog thereof. The word "analog" is used here to mean that a contemplated compound has the same atom-to-atom bonds as does a 1-deoxy-1-(purinyl or pyrimidyl) derivative of fructose, but has stereochemistry about the various ring carbons that differs from that of fructose.

Because such a compound contains a purine or pyrimidine bonded to a hydroxylated furanose ring as is the case of a nucleoside, and can contain a phosphate group bonded to a hydroxymethyl group as does a 5-phosphorylated nucleoside (nucleotide), a contemplated compound can also be viewed as being an analog of a nucleoside or nucleotide, and will generally be described as a nucleoside or nucleotide analog for ease of discussion. In the case of such a contemplated phosphate compound, the phosphate group is at the 6'-position of the sugar ring so that a contemplated compound is a nucleoside analog or a nucleoside analog 6'-phosphate.

A contemplated nucleoside analog and its 6'-phosphate correspond in structure to a compound shown by structural Formula I, below,

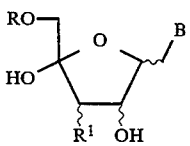

I wherein R is hydrogen or $PO_3^=M^{+2}$, and $R^1$ is hydrogen or hydroxyl, with hydroxyl being preferred.

Where $R^1$ is a preferred hydroxyl group, structural Formula I becomes structural Formula II, shown below.

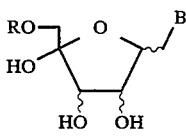

II

In the above structural formulas, and in all other chemical structures shown herein, B is a purine or pyrimidine base. Being nucleoside analogs, those purine and pyrimidine bases are each bonded via the ring nitrogen to which they would normally be bonded to a ribosyl or deoxyribosyl group. For the purines, that bonding occurs via the 9-position nitrogen atom, whereas for the pyrimidines, that bonding is via the 1-position nitrogen atom. The bonding for exemplary pyrimidines and purines is shown in the structures below wherein the unfilled valence is in the bonding position.

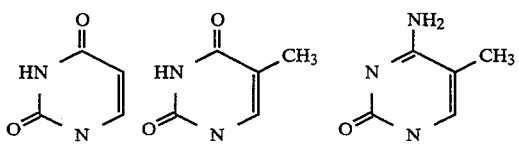

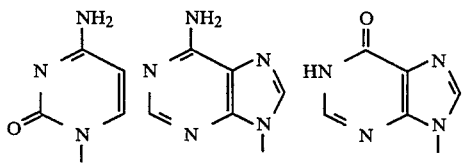

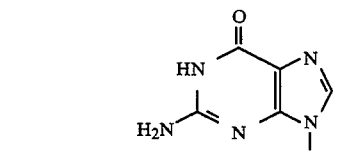

In further reference to structural Formulas I and II, and the other structures shown herein, wavy lines are used to show both configurations of the bonded group. Bonds directed upwardly are intended to project above the plane of a depicted ring and those directed downwardly are intended to project below a depicted ring. Darkened wedge-shaped bonds are similarly intended to project above a depicted ring, whereas dashed wedge-shaped bonds are intended to project below a depicted ring. Hydrogen atoms not required to show stereochemistry or required as part of a substituent group such as a hydroxyl are not shown.

$M^{+2}$ in structural Formulas I and II and other formulas herein is a mono- or divalent cation whose charge is equivalent to that of the phosphate group shown. Exemplary of such cations are the proton, an alkali metal ion such as sodium or potassium, an alkaline earth metal ion such as calcium or magnesium, an ammonium ion ($NH_4^+$) or $C_1$-$C_6$ mono-, di-, tri- or tetraalkyl ammonium ion as are well known. Exemplary $C_1$-$C_6$ alkyl groups are discussed hereinafter.

A compound of structural Formulas I or II can be named in several ways. In one way, they are named as a derivative of the furanose. In another, they are named as a derivative of the purine or pyrimidine, as are nucleosides and nucleotides. For example, particularly preferred Compounds 6 and 5, whose structural formulas are shown hereinbelow where A is adenine, can be named as 6-adenyl-6-deoxy-L-sorbose and 6-adenyl-6-deoxy-D-fructose, respectively. Alternatively, those same compounds can be named 9,1'-homo-β-(5'-hydroxyarabino)adenine and 9,1'-homo-α-(5'-hydroxyarabino)adenine. The corresponding phosphates can be similarly named.

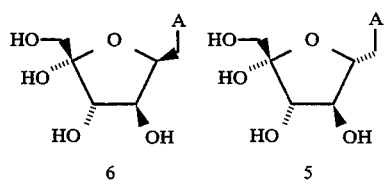

Compounds 5 and 6 can be depicted together by structural Formula III, below. A 6'-phosphate nucleotide analog is generically shown in structural formula IV, below, where $M^{+2}$ and $R^1$ are as before defined.

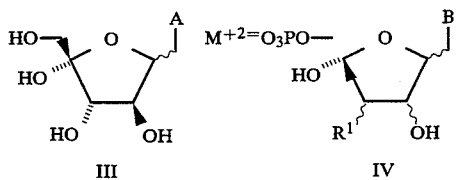

A compound of the invention is useful as an inhibitor of a DNA polymerase or nucleoside phosphylase enzyme. In addition, the 5'-hydroxyl group adjacent to the hydroxymethyl group of Compounds 5 or 6, for example, can be removed and replaced by a hydrogen by well known free radical chemistry to form nucleoside analogs having three hydroxyls on the furanose ring that are more similar in structure to naturally occurring nucleosides. Those 5'-deoxy compounds can be utilized in place of a usual nucleotide 5'-phosphate preparing oligo- or polynucleotides for use in hybridization studies.

Compound Preparation

A compound described before is prepared by the use of an aldolase enzyme. The choice of aldolase provides the stereochemistry about the 3'- and 4'-positions, counting from the purine- or pyrimidine-bonded methylene.

Aldolases are a class of enzymes with flexible acceptor specificity that provide stereospecific aldol condensation products. Fructose-1,6-diphosphate (FDP) aldolase, for example, catalyzes the stereospecific condensation of dihydroxyacetone phosphate (DHAP, Compound 1) as donor substrate and D-glyceraldehyde-3-phosphate (G-3P) as acceptor substrate to give fructose-1,6-diphosphate. Midelfort et al., *Biochemistry* 15:2178 (1976). The enzyme accepts a wide variety of aldehyde acceptors to form products stereospecifically with the D-threo (3S,4R) stereochemistry (3'- and 4'-positions as above). Wong, *Science*, 244:1145 (1989); Wong, *CHEMTRACTS*, 3:91 (1990); Drueckhammer et al., *Synthesis*, 7:499 (1991); Bednarski et al., *J. Am. Chem. Soc.*, 111:627 (1989); Toone et al., *Tetrahedron*, 45:5365 (1989).

Use of DHAP as a donor co-substrate provides hydroxyl groups at the 3'- and 4'-positions of a preferred nucleoside analog shown in structural Formula II. On the other hand, use of hydroxyacetone monophosphate [HAMP; $=O_3POCH_2C(O)CH_3$] in place of DHAP provides the 4'-deoxy compounds of structural Formulas I and IV where R' is hydrogen, albeit at a relatively slower reaction rate compared to DHAP.

The unusual aldehyde-containing, acceptor co-substrate used here is a 3-purinyl- or 3-pyrimidinyl-2-hydroxypropanal. That aldehyde is illustrated below by structural Formula V, where B is as defined previously, and is typically prepared in situ from the corresponding acetal shown as structural Formula VI wherein B is as defined before and each $R^2$ is the same $C_1$–$C_6$ alkyl group or both $R^2$ groups are an ethylene group.

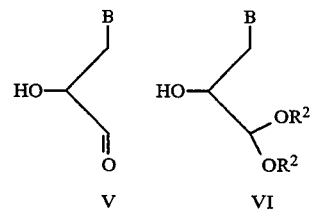

Exemplary $R^2$ alkyl groups and those of a before-discussed alkyl ammonium ion include methyl, ethyl, isopropyl, sec-butyl and hexyl, with ethyl being a preferred $R^2$ group.

A compound of structural Formula VI is itself readily prepared by the base-catalyzed reaction of the corresponding epoxide with the purine or pyrimidine (B) of choice. An exemplary synthesis is provided hereinafter for the adenine derivative.

Exemplary useful aldolases thus include FDP aldolase (EC 4.1.2.3), rhamnulose-1-phosphate (Rham-1-P) aldolase (EC 4.1.2.19), fuculose-1-phosphate (Fuc-1-P) aldolase (EC 4.1.2.17) and tagatose-1,6-diphosphate (TDP) aldolase. These enzymes can be obtained by isolation from cells or tissues and by over-expression techniques. For example, FDP aldolase is usually obtained from rabbit muscle, Rham-1-P aldolase is isolated from *E. coli* strain K-40, Fuc-1-P is obtained from *E. coli* strain K-58 and has been overexpressed [Ozaki et al., *J. Am. Chem. Soc.*, 112:4970 (1990)], and TDP aldolase is obtained from *Lactococcus laetis*, subsp. *lactis*.

The principal α- and β-anomers produced by each of the above enzymes are illustrated hereinbelow, using DHAP as donor co-substrate for a compound of structural Formula V as acceptor co-substrate.

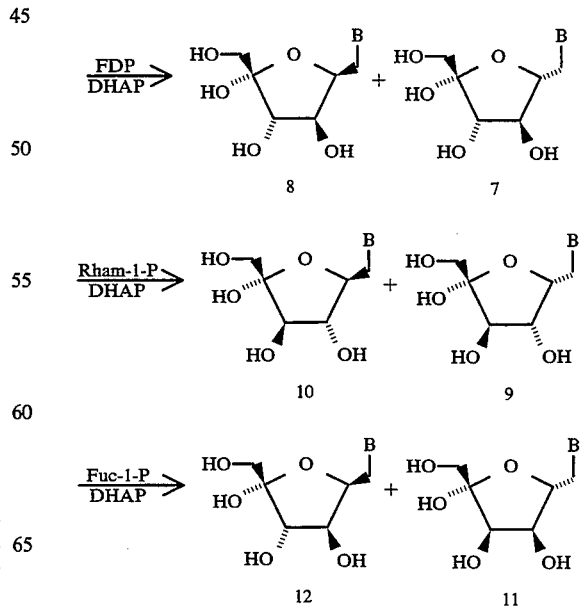

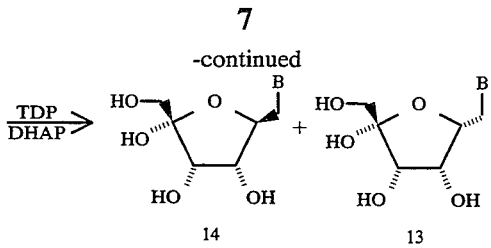

One of the purinyl- or pyrimidinyl-α-hydroxy aldehyde stereoisomers typically reacts more rapidly than the other isomer. As a result, when the products are obtained under kinetic control, one of the two products shown above for each enzyme typically predominates over the other product. For example, using FDP aldolase, the D-isomer with a configuration related to the natural G-3P substrate acceptor generally reacted faster than did the L-isomer to form preferentially a kinetic product of the D-fructofuranose type structure; i.e., Compound 5. The L-sorbose type product (Compound 6) was obtained as a minor product. However, Compound 6 was prepared in high yield using the enantiomerically pure L-aldehyde as substrate acceptor.

To prepare a contemplated compound, the 3-(purinyl or pyrimidinyl)-2-hydroxypropanal acceptor and DHAP or HAMP and a catalytically effective amount of a desired aldolase enzyme are admixed in an aqueous medium to form a reaction mixture. That reaction mixture is maintained for time period sufficient for the corresponding nucleotide analog phosphate to form. The resulting nucleotide analog phosphate can be recovered, and used as such, or hydrolyzed in situ by the addition of a phosphatase enzyme such as acid or basic phosphatase to provide the corresponding nucleoside analog, which is then typically recovered. Other well known methods of phosphate group cleavage can also be used to remove the phosphate group. DHAP is a preferred donor substrate.

The aqueous medium utilized is familiar to those skilled in the art. That medium can be tap water, distilled or deionized water or more preferably a buffered solution whose pH value is chosen to permit the enzyme to function, preferably at its maximum rate.

Such media, including appropriate buffers, pH values and reaction temperature (conditions) are well known to those skilled in the art and need not be gone into in detail here. Illustratively, those conditions include a temperature range of about zero degrees C to about 45° C., a pH value range of about 5 to about 9 and an ionic strength varying from that of distilled water to that of about one molar sodium chloride.

The donor and acceptor co-substrates can be used in equal amounts or one can predominate over the other by 10-fold or more. For example, the aldehyde acceptor co-substrate was used in a four-fold excess in the illustrative preparation discussed hereinafter to help obtain the kinetically preferred product, Compound 5.

The aldolase enzyme is a catalyst, and as such is not consumed during the aldol condensation reaction between donor and acceptor. Thus, a relatively small amount of enzyme can be used to convert a relatively large amount of donor and acceptor. If more product is desired in a given time, one simply adds more catalyst, up to and including a stoichiometric amount, which amount is wasteful.

The actual amount of enzyme in protein weight or international units is often not specified in published papers as the above facts are known to skilled workers who can adjust the amount of catalyst used to their own needs. A catalytic amount of aldolase enzyme is thus defined herein as that amount used to form a desired amount of product in a desired time period at room temperature and atmospheric pressure.

Reaction times typically vary from hours to days. For preparative reactions, one to about seven days are commonly utilized at ambient room temperature (about 200°–220° C.).

Recovery procedures are typically those utilized for the preparation of nucleotides and nucleosides and are also well known to skilled workers. Chromatographic techniques such as HPLC are typically the separation and recovery techniques of choice.

Results

The racemic aldehyde component (Compound 4) used in this kinetically controlled enzymatic synthesis was obtained as shown in Scheme 1, below, and then used to prepare Compounds 5 and 6, as is also shown in Scheme 1.

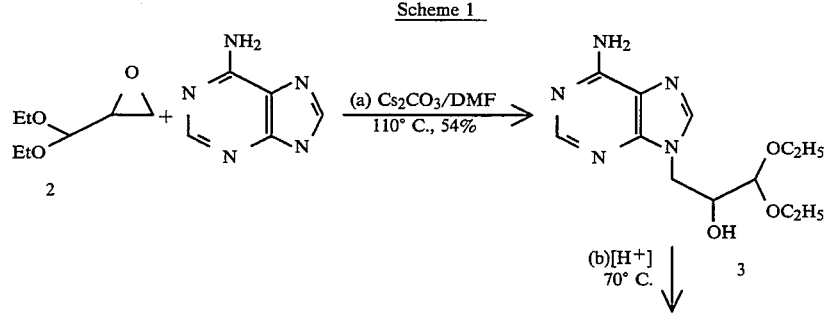

Scheme 1

-continued

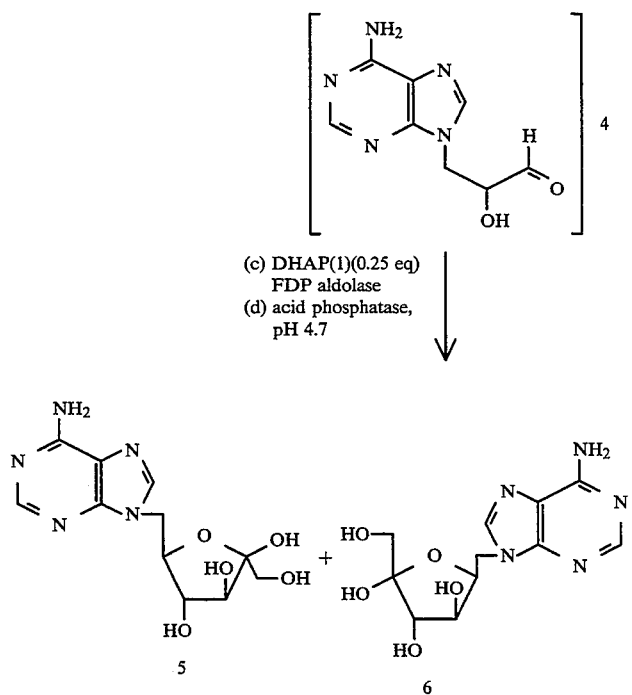

Thus, glycidaldehyde diethyl acetal (Compound 2) [von der Osten et al., *J. Am. Chem. Soc.*, 111:3924 (1989)], was treated with adenine in the presence of cesium carbonate as a base to generate 3-adenyl-2-hydroxypropanal diethyl acetal (Compound 3) in 54 percent yield as step (a). The protected aldehyde was hydrolyzed to form the free aldehyde (Compound 4) in situ in step (b). DHAP [Pederson et al., *Tetrahedron*, 47:2643 (1991)] was added, the solution was neutralized to pH 7, and FDP aldolase from rabbit muscle was then added and the solution was stirred slowly at room temperature in step (c). After the reaction was complete, the phosphate moiety was removed in step (d) with acid phosphatase in situ to afford 6-adenyl-6-deoxy-D-fructose (Compound 5) in 20 percent yield.

In this representative reaction, 4 equivalents of aldehyde were used to obtain the kinetically preferred product Compound 5. The minor product 6-adenyl-6-deoxy-L-sorbose (Compound 6), was obtained in <10 percent of the product mixture, whereas Compound 5 was >90 percent of the product mixture.

The syntheses of Compounds 6 and 15 are shown in Scheme 2, below. For Compound 6, enantiomerically pure Compound (S)-3 (97 percent ee) was prepared from Compound (S)-2 [Pederson et al., *J. Org. Chem.*, 55:4897 (1990)], and used to prepare the substrate for the enzymatic reaction (Scheme 2, 33 percent yield). Otherwise, steps (a–d) of Scheme 1 were followed.

In a separate synthesis, Compound (S)-4 was further reduced with sodium borohydride (step e) to form (S)-3-adenyl-1,2-propanediol (Compound 15), an analog of the biologically active compound 9-(3,4-dihydroxybutyl)guanine. Dateman, et al., *Chem. Scr.*, 26:49 (1986).

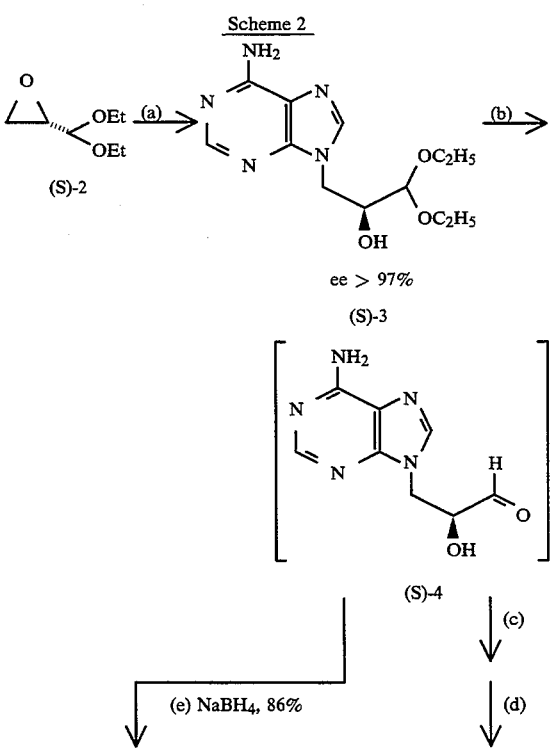

Scheme 2

-continued
Scheme 2

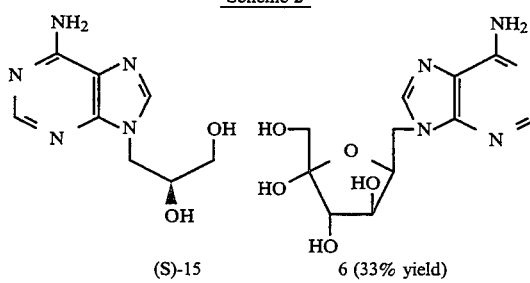

(S)-15    6 (33% yield)

BEST MODE FOR CARRYING OUT THE INVENTION

EXAMPLE 1

3-Adenyl-2-hydroxypropanal Diethyl Acetal (Compound 3)

To a 100 mL round-bottomed flask containing 25 mL of anhydrous dimethylformamide (DMF), 743.5 mg (5.5 mmole) adenine and 584 mg (4 mmole) glycidaldehyde diethyl acetal (Compound 2) were added 1.4 g (4.3 mmole) of cesium carbonate. The solution was stirred at 100° C. for 3.5 hours. The precipitate was filtered off and the solvent was removed under reduced pressure. The remaining residue was purified with silica gel column chromatography ($CHCl_3$:MeOH=18:1) to yield 600 mg (54 percent yield) 3-adenyl-2-hydroxypropanal diethyl acetal (Compound 3) $R_f$=0.37 ($CHCl_3$:MeOH=6:1) $^1$H-NMR ($CD_3OD$) δ1.17–1.24 (6H, m), 3.57–3.64 (4H, m), 3.97 (1H, ddd, J=3.5, 5, 8.5 Hz), 4.20 (1H, dd, J=8.5, 14 Hz), 4.43 (1H, d, J=5 Hz), 4.48 (1H, dd, J=3.5, 14 Hz), 8.10 (1H, s), 8.19 (1H, s) ppm. $^{13}$C-NMR ($CD_3OD$) δ15.57, 15.62, 46.61, 64.5, 65.1, 71.2, 105.0, 119.6, 143.89, 149.3, 153.1, 156.148 ppm. HRMS (M+Na+) calcd 304.1386, found 304.1386.

Compound (S)-3 was similarly prepared from Compound (S)-2 without racemization. $[\alpha]_D^{23}$−31.3 (C 2.3, MeOH), ee >97 percent. The enantiomeric excess of Compound (S)-3 was determined to be greater than 97 percent ee after conversion to the corresponding acetate which was analyzed by $^1$H-NMR in the presence of Eu(hfc)$_3$. The relative intensities of the acetoxy groups at 3.04 and 2.85 were used for the percent ee determination.

EXAMPLE 2

6-Adenyl-6-deoxy-D-fructose (Compound 5)

To an aqueous solution of 3-adenyl-2-hydroxypropanal Compound 4, prepared by heating a suspension of racemic 3-adenyl-2-hydroxypropanal diethyl acetal (Compound 3) (843 mg, 3 mmole) in pH 1.0 buffer (20 mL) at 70° C. for 17 hours, was added DHAP (1 mmole), and the solution was adjusted to pH 7 with 10 N NaOH. To this solution FDP aldolase was added, and the mixture was stirred slowly with 90 percent of the DHAP being consumed. The solution was then adjusted to pH 4.7 and mixed with acid phosphatase (from sweet potatoes, type V, 400 units) at 37° C. for two days. After being neutralized, the solution was lyophilized, and the residue was passed through a short silica gel column in a short time (100 percent MeOH). The solvent was removed under reduced pressure and the residue was applied to a Bio-Gel P-2 column to afford 6-adenyl-6-deoxy-D-fructose (Compound 5) (20 percent) as a white solid. $[\alpha]_D^{23}$=24.50 (c 1, $H_2O$); $^1$H-NMR ($D_2O$) δ3.31–3.38 (2H, m), 3.84–3.96 (3H, m), 4.27 (1H, dd, J=15, 6 Hz), 4.31 (1H, dd, J=15.4 Hz), 7.94 (1H, s), 7.99 (1H, s) ppm. $^{13}$C-NMR ($D_2O$) δ46.47, 63.17, 75.73, 76.20, 78.90, 102.72, 119.5, 143.89, 149.72, 153.1, 156.148 ppm. HRMS (M+Na+) calcd 320.0971, found 320.0971.

EXAMPLE 3

6-Adenyl-6-deoxy-L-sorbose (Compound 6)

Compound 6 was similarly prepared from Compound (S)-3 and purified with Bio-Gel P-2 column in 33 percent yield. $[\alpha]_D^{23}$=−28 (c 1, $H_2O$); $^1$H-NMR ($D_2O$) δ3.45 (1H, d, J=12 Hz), 3.50 (1H, d, J=12 Hz), 4.05 (1H, dd, J=14.5, 9 Hz), 4.13 (1H, d, J=6 Hz), 4.28 (1H, dd, J=14.5, 3 Hz), 4.38–4.44 (2H, m), 7.91 (1H, s), 7.94 (1H, s) ppm. $^{13}$C-NMR ($D_2O$) δ45.37, 63.17, 75.37 (2×C), 76.87, 103.02, 118.61, 143.27, 149.35, 152.67, 155.75 ppm. HRMS (M+H+) calcd 298.1151, found 198.1157.

EXAMPLE 4

(S)-3-Adenyl-1,2-propanediol [Compound (S)-15]

The recovered Compound (S)-4 (37 mg, 0.18 mmole, mainly existing as a dimer) in the previous aldolase-catalyzed aldol condensation was redissolved in $H_2O$ and $NaBH_4$ (15 mg) was added. The solution was stirred at room temperature overnight (about 18 hours). The solvent was evaporated and the residue was purified with silica gel column chromatography ($CHCl_3$:MeOH:HO =7:3:0.4) to provide Compound (S)-15 in 87 percent yield. $[\alpha]_D^{23}$=−24 (c 0.8, $H_2O$); $^1$H-NMR ($D_2O$) δ3.48 (1H, dd, J=12, 6 Hz), 3.59 (1H, dd, J=12, 4.5 Hz), 3.96–3.98 (1H, m), 4.00 (1H, dd, J=14, 8.5 Hz), 4.14 (1H, dd, J=14.3 Hz), 7.83 (1H, s), 7.87 (1H, s) ppm. $^{13}$C-NMR ($D_2O$) δ 47.0, 49.6, 63.6, 70.4, 118.5, 143.3, 149.1, 152.7, 155.6 ppm. HRMS (M+Na+) calcd 210.0991, found 210.0993.

The foregoing is intended as illustrative of the present invention but not limiting. Numerous variations and modifications may be effected without departing from the true spirit and scope of the novel concepts of the invention

We claim:

1. A nucleoside analog of the formula

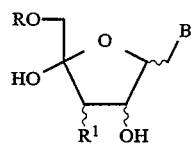

wherein B is purine base attached at the 9-position or pyrimidine base attached at the 1-position, R is hydrogen or $PO_3=M^{+2}$, where $M^{+2}$ is a mono- or divalent cation, and $R^1$ is hydrogen or hydroxyl.

2. The compound according to claim 1 wherein R is hydrogen.

3. The compound according to claim 2 wherein B is adenine.

4. The compound according to claim 3 having the formula, wherein A is adenine,

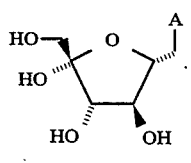
5. The compound according to claim 3 having the formula, wherein A is adenine,
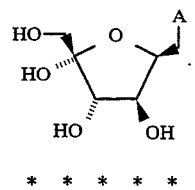
* * * * *